US012636150B2

(12) United States Patent
Montgomery et al.

(10) Patent No.: US 12,636,150 B2
(45) Date of Patent: May 26, 2026

(54) DELIVERY DEVICE HAVING A CONTROL RELEASE SHAFT FOR IMPROVED POSITIONING OF A TRANSCATHETER HEART VALVE

(71) Applicant: MEDTRONIC, INC., Minneapolis, MN (US)

(72) Inventors: Stephen Montgomery, Galway (IE); Padraigh Jennings, Summerhill (IE)

(73) Assignee: MEDTRONIC, INC., Minneapolis, MN (US)

( * ) Notice: Subject to any disclaimer, the term of this patent is extended or adjusted under 35 U.S.C. 154(b) by 736 days.

(21) Appl. No.: 17/999,123

(22) PCT Filed: May 27, 2021

(86) PCT No.: PCT/US2021/034417
§ 371 (c)(1),
(2) Date: Nov. 17, 2022

(87) PCT Pub. No.: WO2021/247350
PCT Pub. Date: Dec. 9, 2021

(65) Prior Publication Data
US 2023/0210659 A1     Jul. 6, 2023

Related U.S. Application Data

(60) Provisional application No. 63/033,950, filed on Jun. 3, 2020.

(51) Int. Cl.
*A61F 2/24* (2006.01)
*A61F 2/95* (2013.01)
*A61F 2/966* (2013.01)

(52) U.S. Cl.
CPC .......... *A61F 2/2436* (2013.01); *A61F 2/9517* (2020.05); *A61F 2002/9534* (2013.01); *A61F 2002/9665* (2013.01)

(58) Field of Classification Search
CPC ...... A61F 2/2436; A61F 2/2418; A61F 2/966; A61F 2/2427; A61F 2/24; A61F 2/2412; A61F 2002/9665; A61F 2002/9534
See application file for complete search history.

(56) References Cited

U.S. PATENT DOCUMENTS

| | | | |
|---|---|---|---|
| 8,147,541 | B2 | 4/2012 | Forster et al. |
| 8,579,963 | B2 | 11/2013 | Tabor |
| (Continued) | | | |

FOREIGN PATENT DOCUMENTS

| | | |
|---|---|---|
| CN | 102196784 A | 9/2011 |
| CN | 102883683 A | 1/2013 |
| (Continued) | | |

OTHER PUBLICATIONS

International Search Report issued Sep. 14, 2021 in Intl Appl. No. PCT/US2021/034417.

(Continued)

*Primary Examiner* — Sarah W Aleman
*Assistant Examiner* — Paris Marie Blass
(74) *Attorney, Agent, or Firm* — MEDLER FERRO WOODHOUSE & MILLS PLLC

(57) ABSTRACT

A delivery device includes a control release shaft and a pusher shaft disposed within the control release shaft. A distal end of the control release shaft includes a collar having a sloped distal edge. The control release shaft is rotatable in order to rotate the collar. The pusher shaft has a distal end having a spindle coupled thereto. The spindle is configured to receive at least one connector extending from at least one endmost crown of the self-expanding prosthesis in order to releasably attach the self-expanding prosthesis to the pusher shaft. When disposed over an end of the self-expanding prosthesis, the collar is configured to radially restrain the endmost crowns and the connector of the self-expanding (Continued)

prosthesis. Actuation of an actuator of the delivery device rotates and proximally retracts the collar relative to the spindle to achieve incremental release of the endmost crowns and the connector of the self-expanding prosthesis.

20 Claims, 9 Drawing Sheets

(56)                    References Cited

U.S. PATENT DOCUMENTS

| | | | |
|---|---|---|---|
| 8,663,302 | B2 | 3/2014 | Schmitt et al. |
| 9,301,839 | B2 | 4/2016 | Stante et al. |
| 9,364,324 | B2 | 6/2016 | Rafiee et al. |
| 9,387,074 | B2 | 7/2016 | Costello |
| 2006/0276872 | A1* | 12/2006 | Arbefeuille ............... A61F 2/89 |
| | | | 623/1.11 |
| 2011/0172765 | A1 | 7/2011 | Nguyen et al. |
| 2011/0251675 | A1* | 10/2011 | Dwork .................. A61F 2/2436 |
| | | | 623/1.26 |

| | | | |
|---|---|---|---|
| 2011/0251676 | A1 | 10/2011 | Sweeney et al. |
| 2011/0257720 | A1 | 10/2011 | Peterson et al. |
| 2012/0035722 | A1 | 2/2012 | Tuval |
| 2012/0301572 | A1 | 11/2012 | Barnes |
| 2014/0039511 | A1 | 2/2014 | Morris et al. |
| 2014/0046429 | A1* | 2/2014 | Cragg ..................... A61F 2/954 |
| | | | 623/1.12 |
| 2016/0175132 | A1 | 6/2016 | Wilger et al. |
| 2016/0250023 | A1 | 9/2016 | Rafiee et al. |

FOREIGN PATENT DOCUMENTS

| | | | |
|---|---|---|---|
| CN | 107896484 | A | 4/2018 |
| CN | 108366857 | A | 8/2018 |
| CN | 110013351 | A | 7/2019 |
| CN | 110177525 | A | 8/2019 |

OTHER PUBLICATIONS

Office Action issued in CN Appl. No. 202180040134.4 on Nov. 20, 2025.

* cited by examiner

DELIVERY DEVICE HAVING A CONTROL RELEASE SHAFT FOR IMPROVED POSITIONING OF A TRANSCATHETER HEART VALVE

FIELD OF THE INVENTION

The present invention is related to delivery devices for and methods of delivering a self-expanding prostheses.

BACKGROUND

Prostheses for implantation in blood vessels or other similar organs of the living body are, in general, well known in the medical art. For example, prosthetic vascular stent-grafts constructed of biocompatible materials have been employed to replace or bypass damaged or occluded natural blood vessels. In general, prosthetic vascular stent-grafts typically include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. Thus, prosthetic vascular stent-grafts are typically held in place by mechanical engagement and friction due to the opposition forces provided by the radially expandable stents. In another example, expandable stents may be deployed without the addition of a covering graft component. Further, prosthetic valves supported by stent structures have also been developed for heart and venous valve replacement.

In general, rather than performing an open surgical procedure that may be traumatic and invasive, prostheses are preferably deployed through a less invasive intraluminal delivery procedure. More particularly, a lumen or vasculature is accessed percutaneously at a convenient and less traumatic entry point, and the prosthesis is routed through the vasculature to the site where the prosthesis is to be deployed. Intraluminal deployment is typically affected using a delivery catheter device with coaxial inner and outer tubes arranged for relative axial movement. For example, a heart valve prosthesis may be compressed and disposed within the distal end of an outer tube or sheath. The delivery catheter is then maneuvered, typically routed through a body lumen until the end of the delivery catheter and the prosthesis are positioned at the intended treatment site. The inner tube or shaft is then held stationary while the outer tube of the delivery catheter is withdrawn. A stop or prosthesis retention member may be utilized to prevent the prosthesis from being withdrawn with the outer tube. As the outer tube is withdrawn, the prosthesis is released from the confines of the outer tube and radially self-expands so that at least a portion of the prosthesis contacts and substantially conforms to a portion of the surrounding interior of the body lumen, e.g., the blood vessel wall or anatomical conduit.

Although transcatheter delivery methods have provided safer and less invasive methods for replacing a defective native heart valve, complications may arise including vessel trauma due to percutaneous delivery within highly curved anatomy and/or due to a large delivery profile of the prosthesis, inaccurate placement of the heart valve prosthesis, conduction disturbances, coronary artery obstruction, and/or undesirable paravalvular leakage and/or regurgitation at the implantation site. More particularly, for example, a prosthesis that is positioned too deep relative to the native annulus or placed unevenly within the native annulus in terms of depth may cause conduction disturbances. In another example, if a prosthesis is not centered relative to the native annulus, the deployed prosthesis may dislodge from the implantation site and/or undesirable paravalvular leakage and/or regurgitation may occur. Thus, it is imperative that the prosthesis be accurately located relative to the native annulus after full deployment of the prosthesis.

Embodiments hereof are directed to a delivery device for a transcatheter valve prosthesis for positioning a valve prosthesis in situ with improved accuracy to address one or more of the aforementioned complications.

SUMMARY

Embodiments hereof relate to a delivery device for percutaneously delivering a self-expanding prosthesis that includes a handle having at least one actuator thereon, a control release shaft, and a pusher shaft disposed within the control release shaft. The self-expanding prosthesis has a first end and a second end, the second end being proximal to the first end when the self-expanding prosthesis is loaded onto the delivery device. The control release shaft has a proximal end operatively coupled to the handle and a distal end including a collar having a sloped distal edge. The control release shaft is rotatable via actuation of the at least one actuator of the handle in order to rotate the collar. The pusher shaft has a proximal end operatively coupled to the handle and a distal end having a prosthesis retention member or spindle coupled thereto. The prosthesis retention member or spindle is configured to receive at least one connector extending from at least one endmost crown of the self-expanding prosthesis in order to releasably attach the self-expanding prosthesis to the pusher shaft. When disposed over the second end of the self-expanding prosthesis, the collar is configured to radially restrain the endmost crowns and the at least one connector of the self-expanding prosthesis. Actuation of the at least one actuator of the handle rotates and proximally retracts the collar relative to the spindle to achieve incremental release of the endmost crowns and the at least one connector of the self-expanding prosthesis.

Embodiments also relate to a system including a self-expanding prosthesis and a delivery device that is configured to percutaneously deliver the self-expanding prosthesis. The self-expanding prosthesis has a first end and a second end, the second end being proximal to the first end when the self-expanding prosthesis is loaded onto the delivery device. The self-expanding prosthesis includes a plurality of endmost crowns at the second end and at least one connector extending from at least one endmost crown. The delivery device includes a handle having at least one actuator thereon, a control release shaft, and a pusher shaft disposed within the control release shaft. The control release shaft has a proximal end operatively coupled to the handle and a distal end including a collar having a sloped distal edge. The control release shaft is rotatable via actuation of the at least one actuator of the handle in order to rotate the collar. The pusher shaft has a proximal end operatively coupled to the handle and a distal end having a prosthesis retention member or spindle coupled thereto. The prosthesis retention member or spindle is configured to receive at least one connector extending from at least one endmost crown of the self-expanding prosthesis in order to releasably attach the self-expanding prosthesis to the pusher shaft. When disposed over the second end of the self-expanding prosthesis, the collar is configured to radially restrain the endmost crowns and the at least one connector of the self-expanding prosthesis. Actuation of the at least one actuator of the handle rotates and proximally retracts the collar relative to the spindle to achieve incremental release of the endmost crowns and the at least one connector of the self-expanding prosthesis.

Embodiments hereof also relate to a delivery device for percutaneously delivering a self-expanding prosthesis that includes a handle having at least one actuator thereon, an outer sheath, a control release shaft disposed within the outer sheath, a pusher shaft disposed within the control release shaft, and an inner shaft disposed within the pusher shaft, the inner shaft having a distal portion that is configured to receive the self-expanding prosthesis thereon. The self-expanding prosthesis has a first end and a second end, the second end being proximal to the first end when the self-expanding prosthesis is loaded onto the delivery device. The outer sheath includes a proximal end operatively coupled to the handle and a distal portion that is configured to compressively restrain the self-expanding prosthesis during delivery. The outer sheath is retractable relative to the self-expanding prosthesis. The control release shaft has a proximal end operatively coupled to the handle and a distal end including a collar having a sloped distal edge. The control release shaft is rotatable via actuation of the at least one actuator of the handle in order to rotate the collar. The pusher shaft has a proximal end operatively coupled to the handle and a distal end having a prosthesis retention member or spindle coupled thereto. The prosthesis retention member or spindle is configured to receive at least one connector extending from at least one endmost crown of the self-expanding prosthesis in order to releasably attach the self-expanding prosthesis to the pusher shaft. When disposed over the second end of the self-expanding prosthesis, the collar is configured to radially restrain the endmost crowns and the at least one connector of the self-expanding prosthesis. Actuation of the at least one actuator of the handle rotates and proximally retracts the collar relative to the spindle to achieve incremental release of the endmost crowns and the at least one connector of the self-expanding prosthesis.

Embodiments hereof also relate to a method of delivering a heart valve prosthesis to a treatment site within a body lumen. A delivery device having the heart valve prosthesis loaded thereon is advanced through a vasculature. The heart valve prosthesis has a first end and a second end, the second end being proximal to the first end when the heart valve prosthesis is loaded onto the delivery device. The delivery device includes a control release shaft having a distal end including a collar with a sloped distal edge. The heart valve prosthesis includes a plurality of endmost crowns at the second end thereof, a first connector extending from at least one of the plurality of endmost crowns, and a second connector extending from another at least one of the plurality of endmost crowns. The first and second connectors are coupled to a prosthesis retention member or spindle of the delivery device and the heart valve prosthesis is held in a radially compressed configuration within an outer sheath of the delivery device. The heart valve prosthesis is positioned at the treatment site. The outer sheath of the delivery device is retracted to expose the first end of the heart valve prosthesis, thereby allowing the first end of the heart valve prosthesis to radially expand. The outer sheath of the delivery system is further retracted to expose the second end of the heart valve prosthesis. The collar of the control release shaft radially restrains the endmost crowns and the first and second connectors of the heart valve prosthesis such that the first and second connectors of the heart valve prosthesis remain coupled to the spindle of the delivery device after the outer sheath is retracted. At least one actuator of the delivery device is rotated to proximally retract the collar relative to the spindle to release the first connector of the heart valve prosthesis from the delivery device. The collar of the control release shaft radially restrains at least the second connector of the heart valve prosthesis after the first connector is released such that the second connector of the heart valve prosthesis remains coupled to the spindle of the delivery device after the first connector is released. The at least one actuator of the delivery device is further rotated to proximally retract the collar relative to the spindle to release the second connector of the heart valve prosthesis from the delivery device, thereby allowing the second end of the heart valve prosthesis to radially expand.

BRIEF DESCRIPTION OF THE DRAWINGS

The accompanying figures, which are incorporated herein, form part of the specification and illustrate embodiments of a delivery system. Together with the description, the figures further explain the principles of and enable a person skilled in the relevant art(s) to make, use, and implant the prosthesis described herein. In the drawings, like reference numbers indicate identical or functionally similar elements.

DETAILED DESCRIPTION OF THE INVENTION

Figure 1:
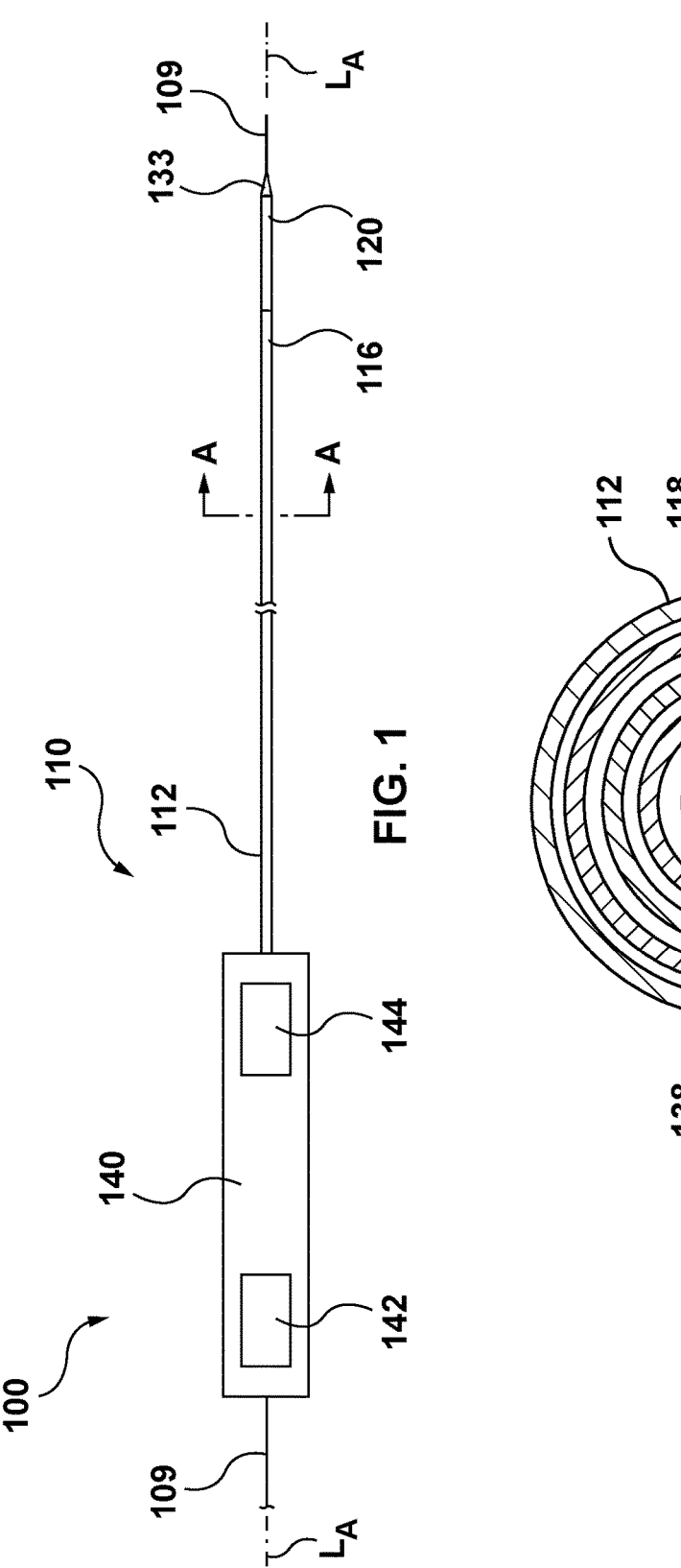
FIG. 1 is a side view of a delivery system according to an embodiment hereof, wherein the delivery system includes a delivery device and a self-expanding prosthesis, the self-expanding prosthesis being shown in a delivery configuration.

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive illustrative self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynor-bornene, trans-polyisoprene, styrene-butadiene, and poly-urethane. As well poly L-D lactic copolymer, oligo capry-lactone copolymer and poly cyclo-octine can be used separately or in conjunction with other shape memory polymers.

The following detailed description is merely illustrative in nature and is not intended to limit the invention or the application and uses of the invention. Although the description of embodiments hereof are in the context of delivery systems for delivering a heart valve prosthesis within a native aortic valve, the delivery systems of the invention can also be used in other areas of the body, such as for delivering a heart valve prosthesis within a native mitral valve, for delivering a heart valve prosthesis within a native pulmonic valve, for delivering a heart valve prosthesis within a native tricuspid valve, for delivering a venous valve, or for delivering a heart valve prosthesis within a failed previously-implanted prosthesis. Furthermore, there is no intention to be bound by any expressed or implied theory presented in the preceding technical field, background, brief summary or the following detailed description.

Embodiments hereof relate to a delivery device for per-cutaneously delivering a self-expanding prosthesis with improved positioning accuracy. The self-expanding prosthesis has a first end and a second end, the second end being proximal to the first end when the self-expanding prosthesis is loaded onto the delivery device. The delivery device includes a control release shaft that controls release or deployment of the second end of a self-expanding prosthesis. Additional restraint of the second end of the self-expanding prosthesis improves positioning accuracy due to the fact that after being positioned at a target location by a clinician, the self-expanding prosthesis may move away from the target location in situ when the second end of the self-expanding prosthesis is released from the delivery device. Particularly, due to the kinetic energy stored up within the second end of the self-expanding prosthesis when released, the self-expanding prosthesis may move or tilt when fully deployed or released from the delivery device which is undesirable. Embodiments hereof relate to control-ling the release of connectors attached to the second end of the self-expanding prosthesis such that the connectors are released in a gradual or incremental matter. The control release shaft is configured to release the connectors gradu-ally and incrementally to offset the effect of the frame expansion force. As will be explained in more detail herein, the control release shaft is rotatable such that when the control release shaft rotates or turns, the control release shaft simultaneously retracts due to the operation of an actuator of a handle at the proximal end of the delivery device, and as a result thereof the connectors individually and sequentially disengage or detach from the delivery device. The speed that the connectors are released from the delivery device is controlled by the rate of rotation of the control release shaft, therefore slowing the final step of deployment of the self-expanding prosthesis and further preventing uncontrolled release of the self-expanding prosthesis from the delivery device. The second end of the self-expanding prosthesis is thus selectively held, restrained, or otherwise controlled by the control release shaft to ensure accurate positioning of the self-expanding prosthesis when the second end of the self-expanding prosthesis is released from the delivery device during the final step of deployment.

Figure 1A:
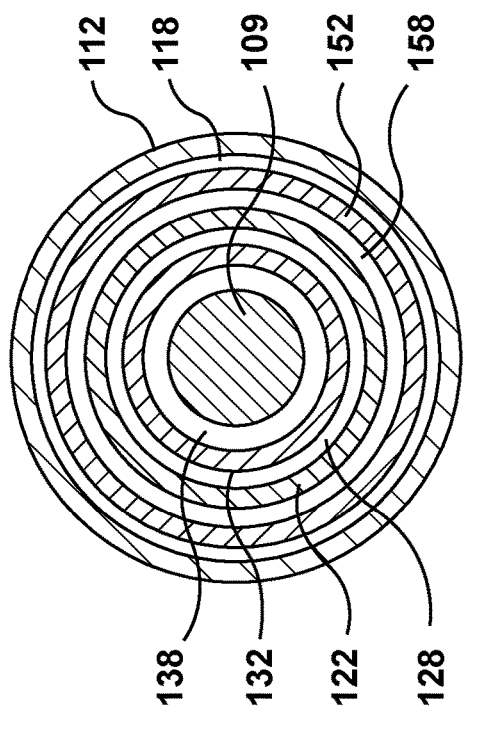
FIG. 1A is a cross-sectional view of the delivery system of FIG. 1 taken along line A-A of FIG. 1.
Figure 1B:
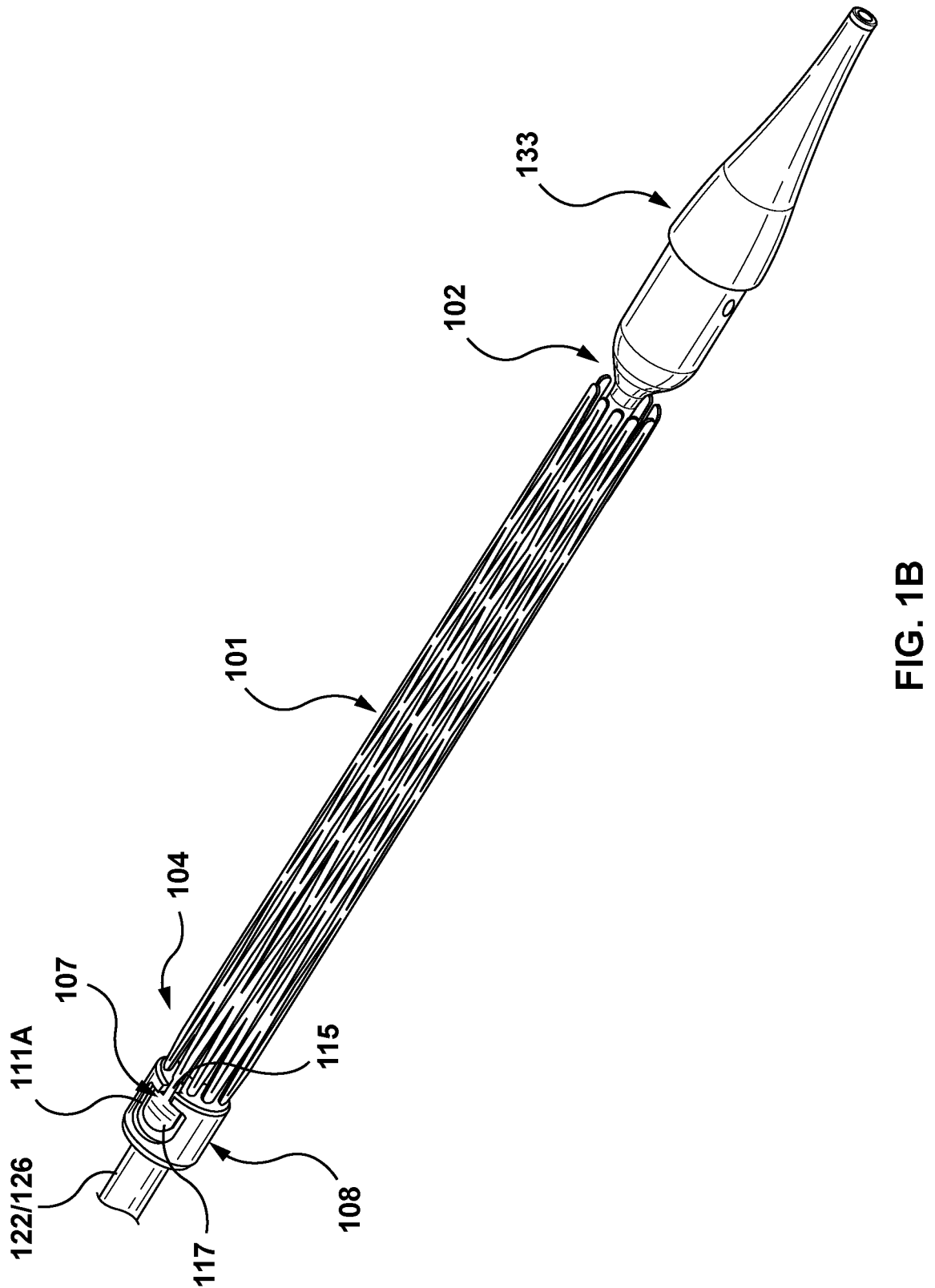
FIG. 1B is a perspective view of a distal portion of the delivery system of FIG. 1, wherein the self-expanding prosthesis is in the delivery configuration and an outer sheath and a control release shaft of the delivery device are not shown for illustrative purposes only.
Figure 2:
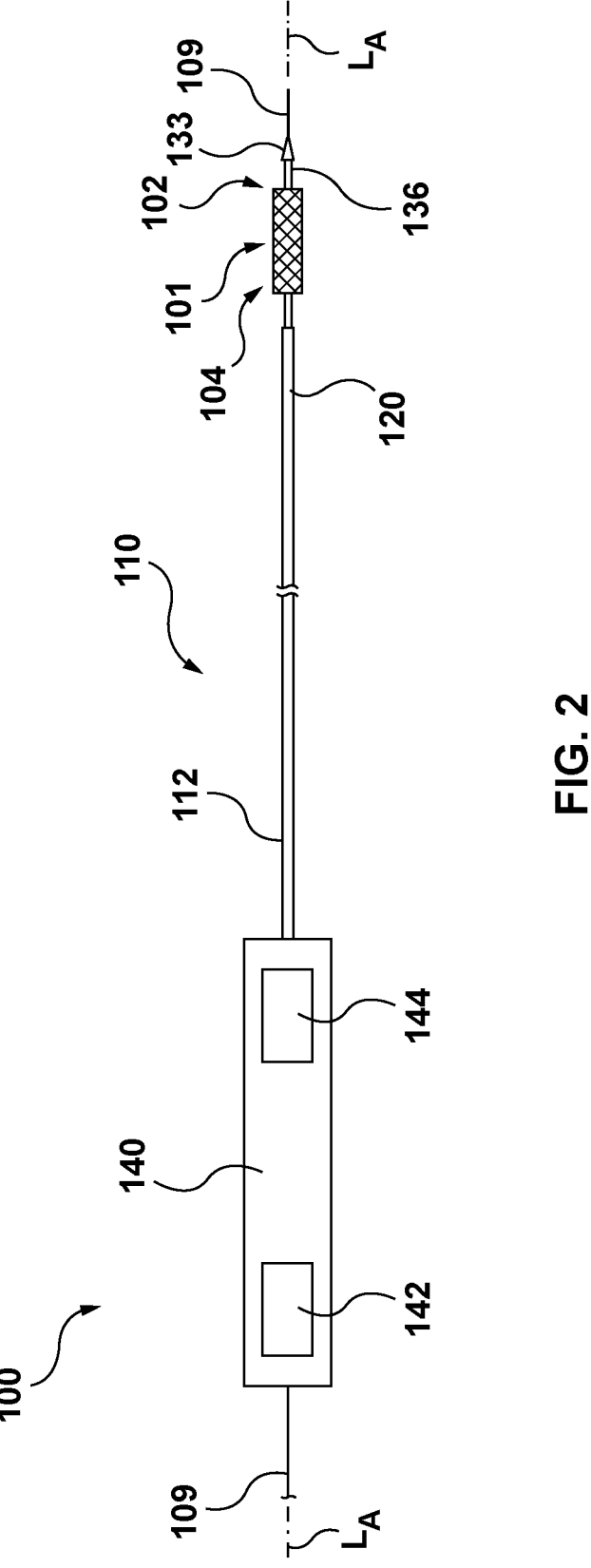
FIG. 2 is a side view of the delivery system of FIG. 1, wherein the self-expanding prosthesis is in a deployed configuration.

The delivery system will be described in more detail with reference to the figures. A delivery system 100 includes a self-expanding prosthesis 101 and a delivery device 110 configured to percutaneously deliver the self-expanding prosthesis 101 with improved positioning accuracy. The self-expanding prosthesis 101 has a first end 102 and a second end 104, the second end 104 being proximal to the first end 102 when the self-expanding prosthesis 101 is loaded onto the delivery device 110. More particularly, the delivery system 100 is shown in FIGS. 1, 1A, 1B, and 2. FIG. 1 is a side view of the delivery system 100 in which an outer sheath 112 thereof surrounds and constrains the self-expanding prosthesis 101 (not shown in FIG. 1A) in a radially compressed or delivery configuration. FIG. 1A is a cross-sectional view taken along line A-A of FIG. 1A. FIG. 1B is a perspective view of a distal portion of the delivery system 100 but with the outer sheath 112 and a control release shaft 152 of the delivery device 110 not shown for illustrative purposes only. FIG. 2 is a side view of the delivery system 100 after the outer sheath 112 has been retracted to allow the self-expanding prosthesis 101 to self-expand and the self-expanding prosthesis 101 has been released from the control release shaft 152 to a fully deployed or expanded configuration. The delivery device 110 includes a handle 140 having a first actuator 142 for rotating the control release shaft 152 as will be explained in more detail herein and a second actuator 144 for manipulating the outer sheath 112 as will be explained in more detail herein. The handle 140 can have any shape or size appropriate for convenient handling by a user.

In addition to the outer sheath 112 operatively coupled to the handle 140, the delivery device 110 further includes the control release shaft 152 disposed within the outer sheath 112, a pusher shaft 122 disposed within the control release shaft 152, and an inner shaft 132 disposed within the pusher shaft 122. The outer sheath 112, the control release shaft 152, the pusher shaft 122, and the inner shaft 132 each distally extend from within the handle 140.

The outer sheath 112 has a proximal end (not shown) which terminates within and is operatively coupled to the handle 140 and a distal end 116. As best shown in FIG. 1A, the outer sheath 112 defines a lumen 118 and is slidingly and concentrically disposed over the control release shaft 152. As used herein, "slidably" denotes back and forth movement in a longitudinal direction along or generally parallel to a central longitudinal axis $L_A$ of the delivery system 100. A distal portion of the outer sheath 112 defines a capsule 120. The capsule 120 is configured to compressively retain the self-expanding prosthesis 101 in a collapsed configuration for delivery to the desired treatment location. While the capsule 120 is described herein as a distal portion of the outer sheath 112, the capsule 120 may be a separate component coupled to the distal end of the outer sheath 112. Moreover, although the outer sheath 112 is described herein as a single component, this is not meant to limit the design, and the outer sheath 112 may include components such as, but not limited to a proximal shaft or other components suitable for the purposes described herein.

The second actuator 144 of the handle 140 is configured for retracting the capsule 120. The second actuator 144 is coupled to the outer sheath 112, and is generally constructed to provide selective proximal retraction and distal advancement of the outer sheath 112, and particularly of the capsule 120 attached thereto, relative to the self-expanding prosthesis 101 held in a radially compressed, delivery configuration therein for covering and uncovering the self-expanding prosthesis 101. The second actuator 144 may assume any construction that is capable of providing the desired sheath actuation functionality, such as those described in U.S. Pat. No. 8,579,963 to Tabor, which is assigned to the same assignee as the present disclosure and which is herein incorporated by reference in its entirety.

Figures 5, 6, 7, 8, 9:
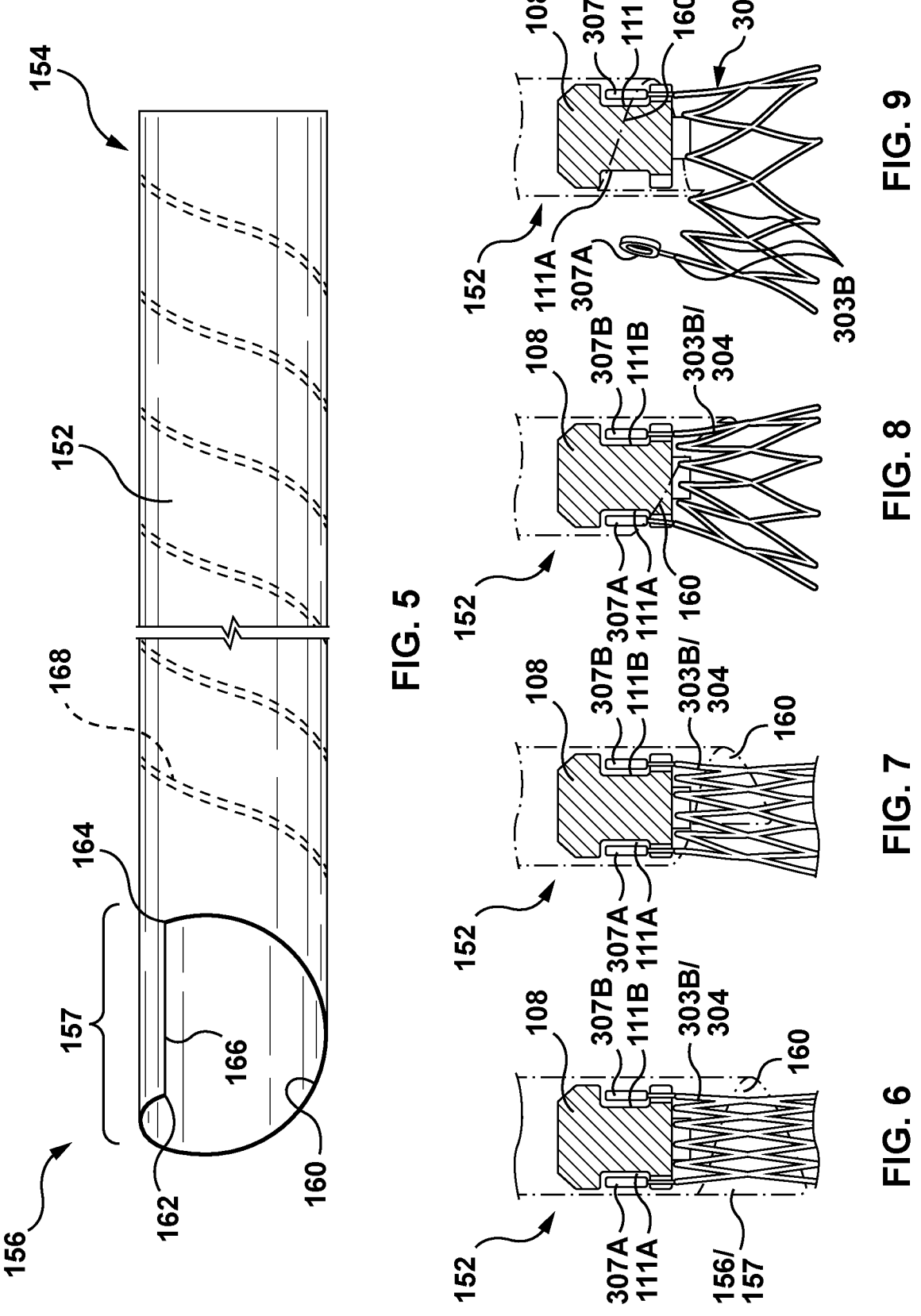
FIG. 5 is a perspective side view of the control release shaft of the delivery device of FIG. 1, wherein the control release shaft is shown removed from the delivery device for illustrative purposes only.
FIG. 6 is an illustration of a distal end of the control release shaft and an end of a self-expanding prosthesis shown removed from the delivery system for illustrative purposes only, wherein the control release shaft is disposed over all endmost crowns of the self-expanding prosthesis.
FIG. 7 is an illustration of a distal end of the control release shaft and an end of a self-expanding prosthesis shown removed from the delivery system for illustrative purposes only, wherein rotation of the control release shaft has been initiated such that some endmost crowns of the self-expanding prosthesis are exposed.
FIG. 8 is an illustration of a distal end of the control release shaft and an end of a self-expanding prosthesis shown removed from the delivery system for illustrative purposes only, wherein rotation of the control release shaft has continued such that all endmost crowns of the self-expanding prosthesis are exposed.
FIG. 9 is an illustration of a distal end of the control release shaft and an end of a self-expanding prosthesis shown removed from the delivery system for illustrative purposes only, wherein rotation of the control release shaft has continued such that one connector of the self-expanding prosthesis is exposed and released from a spindle.

With additional reference to FIG. 5, which is a perspective side view of the control release shaft 152 shown removed from the delivery device 110 for illustrative purposes only, the control release shaft 152 has a proximal end 154 which terminates within and is operatively coupled to the handle 140 and a distal end 156 disposed inside of the outer sheath 112 when the outer sheath 112 is disposed over the self-expanding prosthesis 101. As best shown in FIG. 1A, the control release shaft 152 defines a lumen 158 and is concentrically disposed over the pusher shaft 122. A distal portion of the control release shaft 152 defines a collar 157 having a sloped or angled distal edge 160. The sloped distal edge 160 of the collar 157 is helical and includes a first or distal end 162 and a second or proximal end 164. More particularly, the sloped distal edge 160 of the collar 157 extends proximally from the distal end 162 to the proximal end 164 in a helical path, such that the proximal end 164 is spaced apart in an axial direction from the distal end 162 and thereby forms or defines an axial edge 166 that extends between the proximal end 164 and the distal end 162. The axial edge 166 is a straight or linear edge that extends in a longitudinal direction along or generally parallel to the central longitudinal axis $L_A$ of the delivery system 100. The sloped distal edge 160 curves or winds in a helical path around the central longitudinal axis $L_A$ of the delivery system 100. As will be explained in more detail herein with respect to FIGS. 6-9, the collar 157 is configured to radially restrain the second end 104 of the self-expanding prosthesis 101 until the operator chooses to fully deploy and release the self-expanding prosthesis 101 from the delivery device 110. While the collar 157 is described herein as a distal portion of the control release shaft 152, the collar 157 may be a separate component coupled to the distal end of the control release shaft 152. Moreover, although the control release shaft 152 is described herein as a single component, this is not meant to limit the design, and the control release shaft 152 may include components such as, but not limited to a proximal shaft or other components suitable for the purposes described herein.

The first actuator 142 of the handle 140 is configured for rotating and simultaneously proximally retracting the control release shaft 152. The first actuator 142 is coupled to the proximal end 154 of the control release shaft 152, and provides rotation or torqueing of the control release shaft 152, and particularly of the collar 157 attached thereto, relative to the self-expanding prosthesis 101 for uncovering the second end 104 of the self-expanding prosthesis 101. An exemplary first actuator 142 is shown and described in more detail in FIGS. 16-19.

In order to improve torqueability of the control release shaft 152, a coil 168 may be embedded into a polymeric material of the control release shaft 152. The control release shaft 152 may be formed of one or more polymeric materials, non-exhaustive examples of which include polyethylene, polyethylene block amide copolymer (PEBA), polyamide and/or combinations thereof, either laminated, blended or co-extruded. The coil 168 is a reinforcement layer incorporated within the polymeric material in order to enhance torqueability of the control release shaft 152. The collar 157 is disposed distal to a distal end of the coil 168, and the collar 157 may be formed from the same polymeric material as the control release shaft 152. In another embodiment in which the collar 157 is a separate component attached to a distal end of the control release shaft 152, the collar 157 may be formed from a material that is different than the polymeric material of the control release shaft. In an embodiment, the sloped distal edge 160 of the collar 157 is formed from a reflowed polymer material although other methods of manufacture may be used to shape the sloped distal edge 160.

The pusher shaft 122 is disposed between the control release shaft 152 and the inner shaft 132. As best shown in FIG. 1A, the pusher shaft 122 defines a lumen 128 and is concentrically disposed over the inner shaft 132. The pusher shaft 122 has a proximal end (not shown) which terminates within the handle 140 and a distal end 126 disposed inside of the outer sheath 112 when the outer sheath 112 is disposed over the self-expanding prosthesis 101. The distal end 126 of the pusher shaft 122 includes a prosthesis retention member or spindle 108 which is releasably coupled to an end of the self-expanding prosthesis 101. As best shown on the perspective view of FIG. 1B, having the outer sheath 112 removed for illustrative purposes only, the spindle 108 is a tubular component having at least one recess 111A formed on an outer surface thereof that is configured to receive a connector 107 extending proximally from an endmost crown of the self-expanding prosthesis 101. In an embodiment, the connector 107 is a planar or flat component that includes a stem 115 and a paddle 117. The stem 115 extends between an endmost crown of the self-expanding prosthesis 101 and the paddle 117. The paddle 117 is relatively wider or has a larger width than the stem 115, and is configured or shaped to fit within or mate with the recess 111A of the spindle 108. Although shown with a generally semi-circular configuration, the paddle 117 may have other shapes including circular, rectangular, triangular, or other suitable shape as long as it is configured to fit within or mate with the recess 111A of the spindle 108. As shown in FIGS. 6-9, the spindle 108 includes first and second recesses 111A, 111B at opposing locations for receiving the opposing connectors 107 of the self-expanding prosthesis 101. In another embodiment (not shown), it will be understood by one of ordinary skill in the art that the spindle 108 may include more or fewer than two recesses for receiving a corresponding number of connectors of the self-expanding prosthesis 101. The self-expanding prosthesis 101 includes at least one connector, but may include two or more connectors as described in more detail herein with respect to FIGS. 3-4. Prior to full deployment of the self-expanding prosthesis 101, the collar 157 of the control release shaft 152 radially restrains the endmost crowns and the connectors 107 of the self-expanding prosthesis. As will be explained in more detail herein with respect to FIGS. 6-9, rotation of the control release shaft 152 relative to the spindle 108 rotates and proximally retracts the collar 157 to achieve incremental release of the endmost crowns and the connectors 107 of the self-expanding prosthesis 101.

The inner shaft 132 has a proximal end (not shown) which terminates within the handle 140 and a distal end 136. A tapered flexible nosecone or distal tip 133 may be coupled to the distal end 136 of the inner shaft 132 as shown in FIG. 1 and FIG. 2. As best shown in FIG. 1A which is a cross-sectional view of the delivery system 100 taken along line A-A of FIG. 1, the inner shaft 132 defines a lumen 138 such that the delivery system 100 may be slidingly disposed and tracked over a guidewire 109. The inner shaft 132 may be coupled to the pusher shaft 122 at the spindle 108 such that the inner shaft 132 and the pusher shaft 122 are an assembly.

The inner shaft 132 is configured to receive the self-expanding prosthesis 101 on a distal portion thereof and the outer sheath 112 is configured to compressively retain the self-expanding prosthesis 101 on the distal portion of the inner shaft 132 during delivery, as shown in FIG. 1. Stated another way, the outer sheath 112 surrounds and radially constrains the self-expanding prosthesis 101 in a radially compressed or delivery configuration. As previously described, the distal end 126 of the pusher shaft 122 includes the spindle 108 to which the self-expanding prosthesis 101 is releasably coupled. The self-expanding prosthesis 101 is shown in the view of FIG. 2 but is obscured from view by the outer sheath 112 in FIG. 1. During deployment of the self-expanding prosthesis 101 in situ, the outer sheath 112 is proximally retracted with respect to the self-expanding prostheses 101, thereby incrementally exposing the self-expanding prosthesis 101 until the entire length of the self-expanding prosthesis 101 is fully exposed. However, at this stage of deployment, as will be described in more detail in FIGS. 10-15 herein, the second end 104 of the self-expanding prosthesis 101 is still coupled to the delivery device 110 because the collar 157 of the control release shaft 152 is disposed over the endmost crowns and the connectors 107 of the self-expanding prosthesis 101. The connectors 107 of the self-expanding prosthesis 101 are thus disposed within and coupled to the spindle 108 of the pusher shaft 122. Once positioning of the self-expanding prosthesis 101 is confirmed, the control release shaft 152 is rotated and simultaneously retracted due to operation of the first actuator 142 to individually and incrementally release the connectors 107 from the spindle 108. More particularly, after the sloped distal edge 160 is disposed proximal to recesses 111A, 111B of the spindle 108, the connectors 107 of the self-expanding prosthesis 101 are no longer held within the recesses 111A, 111B of the spindle 108 and the self-expanding prosthesis 101 is permitted to self-expand to its deployed configuration. Thus, once the control release shaft 152 is rotated and retracted to the point that both connectors 107 of the self-expanding prosthesis 101 are released from the spindle 108, the self-expanding prosthesis 101 is fully deployed and released from the delivery device 110. Due to the gradual and controlled release of the second end 104 of the self-expanding prosthesis 101, the self-expanding prosthesis 101 does not move or tilt when the second end 104 thereof is released from the delivery device 110.

Figures 3, 4:
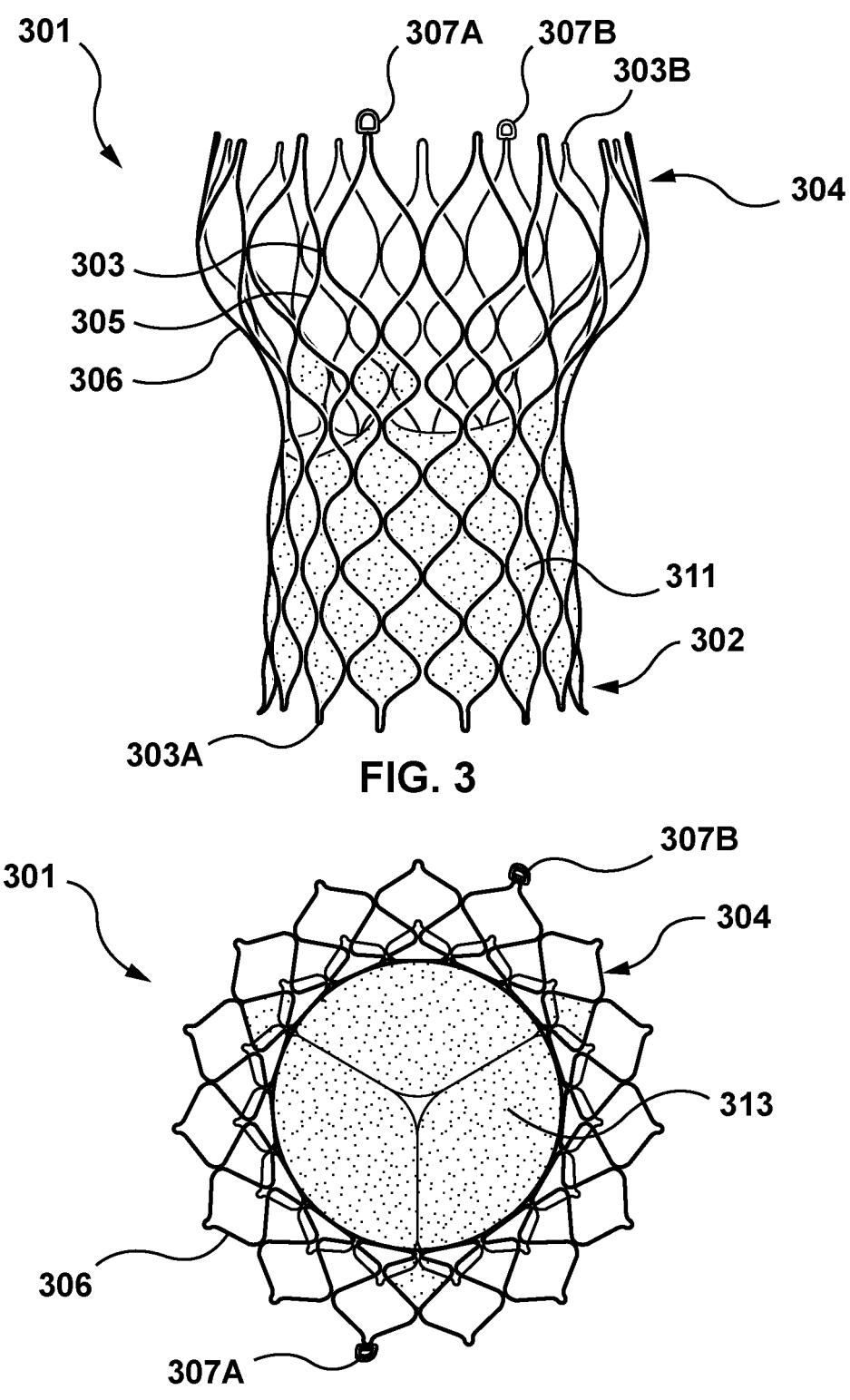
FIG. 3 is a side perspective view of a heart valve prostheses for use in embodiments hereof.
FIG. 4 is an end view of the heart valve prosthesis of FIG. 3.

FIG. 3 and FIG. 4 illustrate side perspective and end views, respectively, of a heart valve prosthesis 301 that may be utilized as the self-expanding prosthesis 101 according to an embodiment hereof. The heart valve prosthesis 301 is merely exemplary and is described in more detail in U.S. Patent Application Pub. No. 2011/0172765 to Nguyen et al., which is herein incorporated by reference in its entirety. It is understood that any number of alternate heart valve prostheses can be used with the delivery devices and methods described herein. In addition, the delivery device 110 may also be used with other self-expanding prostheses such as stent-graft prostheses, uncovered stents, bare metal stents, drug eluting stents, and any self-expanding structure that may move or tilt when the second end thereof is released from the delivery device during deployment.

The heart valve prosthesis 301 includes an expandable stent or frame 306 that supports a prosthetic valve component 313 within the interior of the frame 306. In embodiments hereof, the frame 306 is self-expanding to return to an expanded state from a compressed or constricted delivery state. In the embodiment depicted in FIGS. 3 and 4, the frame 306 has an expanded, longitudinally asymmetric hourglass configuration including a first end or portion 302 and a relatively enlarged second end or portion 304. Each portion of frame 306 may be designed with a number of different configurations and sizes to meet the different requirements of the location in which it may be implanted. When configured as a replacement for an aortic valve, as shown for example in FIGS. 10-15 described in more detail herein, the first end 302 functions as an inflow end of the heart valve prosthesis 301, while the enlarged second end 304 functions as an outflow end of the heart valve prosthesis 301 and is positioned in the patient's ascending aorta. When the heart valve prosthesis 301 is configured as a replacement for an aortic valve and is loaded onto a retrograde delivery system such as delivery system 110, for example, a transfemoral delivery system, a direct or transaortic delivery system, or a subclavian delivery system, the second end 304 is positioned proximal to the first end 302 and deployment of the second end 304 is controlled by the control release sleeve 152. When the heart valve prosthesis 301 is configured as a replacement for an aortic valve and is loaded onto an antegrade delivery system, for example, for a transapical delivery system configured to deliver a prosthesis for replacement for an aortic valve, the second end functions as the inflow end and is positioned proximal to the first end, which functions as the enlarged outflow end. Deployment of the second end is controlled by the control release sleeve 152.

When configured as a replacement for a mitral valve, the inflow end of the heart valve prosthesis 301 is enlarged and is positioned in the patient's left atrium, while the outflow end of the heart valve prosthesis 301 extends into and anchors within the mitral annulus of a patient's left ventricle. When the heart valve prosthesis 301 is configured as a replacement for a mitral valve and is loaded onto a retrograde delivery system such as delivery system 110, the second end 304, which is the outflow end, is positioned proximal to the first end 302, which is the inflow end. Deployment of the second end 304 is controlled by the control release sleeve 152. When the heart valve prosthesis 301 is configured as a replacement for a mitral valve and is loaded onto an antegrade delivery system, for example, a transseptal delivery system or a transatrial delivery system, configured to deliver a prosthesis for replacement for a mitral valve, the second end 304 functions as the enlarged inflow end and is positioned proximal to the first end 302, which functions as the outflow end. Deployment of the second end 304 is controlled by the control release sleeve 152. For example, U.S. Patent Application Publication Nos. 2012/0301572 to Kovalsky et al. and 2012/0035722 to Tuval, each of which are herein incorporated by reference in their entirety, illustrate heart valve prostheses configured for placement in a mitral valve. Each portion of the frame 306 may have the same or different cross-portion which may be for example circular, ellipsoidal, rectangular, hexagonal, rectangular, square, or other polygonal shape, although at present it is believed that circular or ellipsoidal may be preferable when the heart valve prosthesis is being provided for replacement of the aortic or mitral valve. As alternatives to the deployed asymmetric hourglass configuration of FIGS. 3 and 4, the frame 306 may have a symmetric hourglass configuration, a generally tubular configuration, or other stent configuration or shape known in the art for valve replacement.

The frame 306 includes a plurality of diamond-shaped openings that are formed from a plurality of crowns 303 and a plurality of struts 305 with each crown 303 being formed between a pair of opposing struts 305. Each crown 303 is a curved segment or bend extending between opposing struts 305. A plurality of side openings are defined by the plurality of crowns 303 and the plurality of struts 305. A series of endmost crowns 303A are formed at the inflow or first end 302 of the frame 306. The number of endmost crowns 303A may vary according to size and application and may range, for example, between 5-20 crowns. Similarly, a series of endmost crowns 303B are formed at the second end 304 of the frame 306. The number of endmost crowns 303B may vary according to size and application and may range, for example, between 5-20 crowns. In the embodiment of FIGS. 3-4, a first connector 307A extends proximally from a first endmost crown 303B of the heart valve prosthesis 301 and a second connector 307B extends proximally from a second endmost crown 303B of the heart valve prosthesis 301. The first and second connectors 307A, 307B are at opposing locations of the heart valve prosthesis 301 and are configured to be received within the opposing recesses 111A, 111B of the spindle 108 as described above with respect to FIG. 1B.

Although the heart valve prosthesis 301 includes first and second connectors 307A, 307B, it will be understood by one of ordinary skill in the art that the heart valve prosthesis may include more or fewer than two connectors. For example, in an embodiment, a self-expanding prosthesis may include only a single connector extending from an endmost crown thereof. In another embodiment, a self-expanding prosthesis may include three connectors extending from three endmost crowns thereof, with the connectors being equally circumferentially spaced around the second end of the prosthesis. In yet another embodiment, a self-expanding prosthesis may include four connectors extending from four endmost crowns thereof, with the connectors being equally circumferentially spaced around the second end of the prosthesis. A higher number of connectors may further control the final or full release of the endmost crowns. The number of recesses formed on the spindle 108 of the delivery device 110 are equal to the number of connectors extending from the second end of the self-expanding prosthesis.

As previously mentioned, the heart valve prosthesis 301 includes the prosthetic valve component 313 within the interior of frame 306. The prosthetic valve component 313 is capable of blocking flow in one direction to regulate flow there through via valve leaflets that may form a bicuspid or tricuspid replacement valve. FIG. 4 is an end view of FIG. 3 and illustrates an exemplary tricuspid valve having three leaflets, although a bicuspid leaflet configuration may alternatively be used in embodiments hereof. Further, more than three leaflets may be used. Valve leaflets are sutured or otherwise securely and sealingly attached to the interior surface of the frame 306 and/or graft material 311 which encloses or lines the frame 306 as would be known to one of ordinary skill in the art of prosthetic tissue valve construction. Leaflets are attached along their bases to the graft material 311, for example, using sutures or a suitable biocompatible adhesive. Adjoining pairs of leaflets are attached to one another at their lateral ends to form commissures. The orientation of the leaflets within the frame 306 would change depending on which end of the heart valve prosthesis 301 is the inflow end and which end of the heart valve prosthesis 301 is the outflow end, thereby ensuring one-way flow of blood through the heart valve prosthesis 301.

Leaflets may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets include DACRON® polyester commercially available from Invista North America S.A.R.L. of Wilmington, DE, other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

The graft material 311 may also be a natural or biological material such as pericardium or another membranous tissue such as intestinal submucosa. Alternatively, the graft material 311 may be a low-porosity woven fabric, such as polyester, Dacron fabric, or PTFE, which creates a one-way fluid passage when attached to the stent. In one embodiment, the graft material 311 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Turning now to FIGS. 6-9, the operation of the control release shaft 152 and the collar 157 will be described in more detail with respect to deployment of the second end 304 of the heart valve prosthesis 301. FIG. 6 is an illustration of the distal end 156 of the control release shaft 152, the prosthesis retention member or spindle 108, and the second end 304 of the heart valve prosthesis 301 shown removed from the delivery system for illustrative purposes only. At this stage of delivery, the outer sheath 112 and the capsule 120 have been proximally retracted beyond the spindle 108. The control release shaft 152 is still disposed over and radially restrains all endmost crowns 303B of the second end 304 of the heart valve prosthesis 301 until the operator chooses to fully deploy and release the endmost crowns 303B from the delivery device 110. The second end 304 of the heart valve prosthesis 301 is still coupled to the delivery device 110 because the collar 157 of the control release shaft 152 is disposed over the endmost crowns 303B and the connectors 307A, 307B of the heart valve prosthesis 301. The connectors 307A, 307B of the heart valve prosthesis 301 are disposed within the recesses 111A, 111B of the spindle 108.

Once positioning of the self-expanding prosthesis 101 is confirmed, the first actuator 142 is rotated to initiate the deployment process. As shown in FIG. 7, when the operator rotates or turns the first actuator 142, the control release shaft 152 rotates and simultaneously retracts axially in a proximal direction and the sloped distal edge 160 rotates relative to the endmost crowns 303B of the heart valve prosthesis 301. Stated another way, rotation of the first actuator 142 causes the control release shaft 152 to rotate and retract, as explained in more detail with respect to FIGS. 16-19. Due to the operation of the first actuator 142, the control release shaft 152 moves axially or longitudinally when rotated in order to incrementally expose the endmost crowns 303B of the second end 304 of the heart valve prosthesis 301 by the sloped distal edge 160. As the rotation and proximal retraction occurs, the endmost crowns 303B of the second end 304 of the heart valve prosthesis 301 will be exposed as the sloped distal edge 160 passes over individual endmost crowns 303B, thereby uncovering them and allowing them to self-expand. FIG. 7 illustrates the stage at which rotation of the control release shaft 152 has been initiated and some of the endmost crowns 303B of the second end 304 of the heart valve prosthesis 301 are exposed. However, the sloped distal edge 160 is still disposed over and radially restrains most of the endmost crowns 303B of the second end 304 of the heart valve prosthesis 301. Both connectors 307A, 307B of the heart valve prosthesis 301 are disposed within the recesses 111A, 111B of the spindle 108 and are still covered and radially constrained by the control release shaft 152.

In FIG. 8, rotation and proximal retraction of the control release shaft 152 continues such that all of the endmost crowns 303B of the second end 304 of the heart valve prosthesis 301 are exposed or uncovered as the sloped distal edge 160 passes over individual endmost crowns 303B. However, in this embodiment, both connectors 307A, 307B of the heart valve prosthesis 301 are disposed within the recesses 111A, 111B of the spindle 108 and are still covered and radially constrained by the control release shaft 152. Although FIG. 8 depicts all of the endmost crowns 303B exposed while both connectors 307A, 307B of the heart valve prosthesis 301 are still covered by the control release shaft 152, it is possible that one of the connectors 307A, 307B is exposed and permitted to self-expand before all endmost crowns 303B are exposed. The specific order of deployment of the endmost crowns 303B and the connectors 307A, 307B depends upon the placement of the sloped distal edge 160.

The connectors 307A, 307B individually and sequentially disengage or detach from the delivery device 110. In FIG. 9, rotation and proximal retraction of the control release shaft 152 continues until the first connector 307A is exposed or uncovered as the sloped distal edge 160 passes thereover. Once exposed, the first connector 307A is released from the spindle 108 and permitted to self-expand. Endmost crowns 303B adjacent to the first connector 307A are also permitted to self-expand or partially self-expand. Although not shown in FIG. 9, the control release shaft 152 is rotated until both connectors 307A, 307B are released from the spindle 108, thereby also releasing all endmost crowns 303B and permitting all released endmost crowns 303B to self-expand. By incrementally and individually exposing the endmost crowns 303B and connectors 307A, 307B, the release of energy that occurs as the endmost crowns 303B are permitted to self-expand is staggered or spread out. Although FIG. 9 depicts release of the first connector 307A prior to release of the second connector 308B, the order of the connector release may be reversed depending upon the placement of the sloped distal edge 160.

Figures 10, 11, 12:
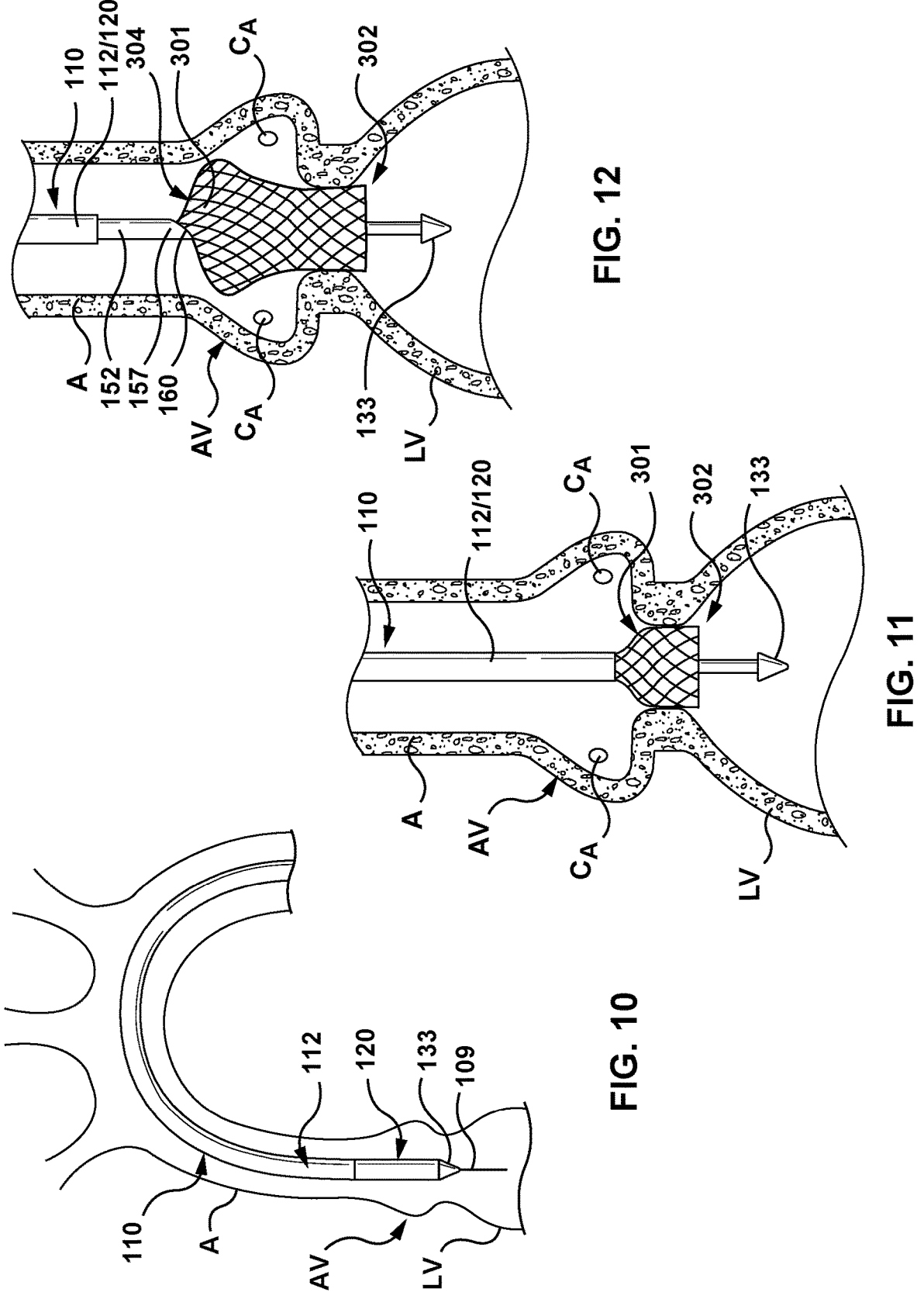
FIG. 10 illustrates a first step of a method of using the delivery device of FIG. 1 to deploy the heart valve prosthesis of FIG. 3, wherein the heart valve prosthesis is shown in the delivery or compressed configuration at the target treatment site.
FIG. 11 illustrates a second step of a method of using the delivery device of FIG. 1 to deploy the heart valve prosthesis of FIG. 3, wherein the heart valve prosthesis is shown being transitioned from the delivery or compressed configuration to the deployed or expanded configuration at the target treatment site.
FIG. 12 illustrates a third step of a method of using the delivery device of FIG. 1 to deploy the heart valve prosthesis of FIG. 3, wherein a full length of the heart valve prosthesis is exposed and the control release shaft is disposed over all endmost crowns of the self-expanding prosthesis.

A method of delivering and deploying the heart valve prosthesis 301 with the delivery device 110 is depicted in FIGS. 10-15. As shown in FIG. 10, in accordance with techniques known in the field of interventional cardiology and/or interventional radiology, the delivery system 100 including the delivery device 110 is transluminally advanced in a retrograde approach through the vasculature to the treatment site, which in this instance is a target diseased native aortic valve AV that extends between a patient's left ventricle LV and a patient's aorta A. Delivery of the delivery system 100 to the native aortic valve AV is accomplished via a percutaneous transfemoral approach in which the delivery system is tracked through the femoral artery, up the aorta and around the aortic arch in order to access the native aortic valve AV. The delivery system 100 may also be positioned within the desired area of the heart via different delivery methods known in the art for accessing heart valves, for example, via a direct aortic delivery method, or a subclavian artery delivery method. As shown, the delivery system 100 is tracked over the guidewire 109 that has previously been inserted into the patient vasculature. During delivery, as the heart valve prosthesis 301 is self-expanding, the heart valve prosthesis 301 remains compressed within the capsule 120 of the outer sheath 112 as the delivery system 100 is manipulated and navigated through the vasculature. The delivery system 100 is advanced until the distal tip 133 thereof is distal to the native aortic valve AV and disposed within the left ventricle LV as shown in FIG. 10, such that the first end 302 of the heart valve prosthesis 301 (which is the inflow end of the heart valve prosthesis 301 when the heart valve prosthesis 301 is configured for placement in a native aortic valve) is positioned at an annulus of a native aortic heart valve.

As shown in FIG. 11, which is a sectional view of the native aortic heart valve AV, the inflow end 302 of the heart valve prosthesis 301 is deployed at the annulus of the native aortic heart valve AV by proximal retraction of the outer sheath 112 and the capsule 120. The outer sheath 112 and the capsule 120 are proximally retracted via the second actuator 144 of the handle 140. At this stage of deployment, positioning of the delivery system 100 may still be adjusted and/or the outer sheath 112 and the capsule 120 may be distally advanced to recapture the heart valve prosthesis 301. For example, in an embodiment, the outer sheath 112 and the capsule 120 may be distally advanced to recapture the heart valve prosthesis 301 until one or more connectors 307A, 307B of the heart valve prosthesis 301 have been released from the spindle 108 of the delivery device 110.

In FIG. 12, the outer sheath 112 and the capsule 120 are fully retracted to expose an entire length of the heart valve prosthesis 301 and the second end 304 of the heart valve prosthesis 301 is still engaged or attached to the spindle 108 of the delivery device 110. More particularly, at this stage of delivery, the outer sheath 112 and the capsule 120 have been proximally retracted beyond the spindle 108. The outer sheath 112 and the capsule 120 are proximally retracted via the second actuator 144 of the handle 140. The collar 157 of the control release shaft 152 is still disposed over and radially restrains all endmost crowns 303B of the second end 304 of the heart valve prosthesis 301. The connectors 307A, 307B of the heart valve prosthesis 301 are disposed within the recesses 111A, 111B of the spindle 108, and the collar 157 is disposed over the connectors 307A, 307B as well as the endmost crowns 303B. At this stage of deployment, the outer sheath 112 and the capsule 120 may be distally advanced to recapture the heart valve prosthesis 301.

Figures 13, 14, 15:
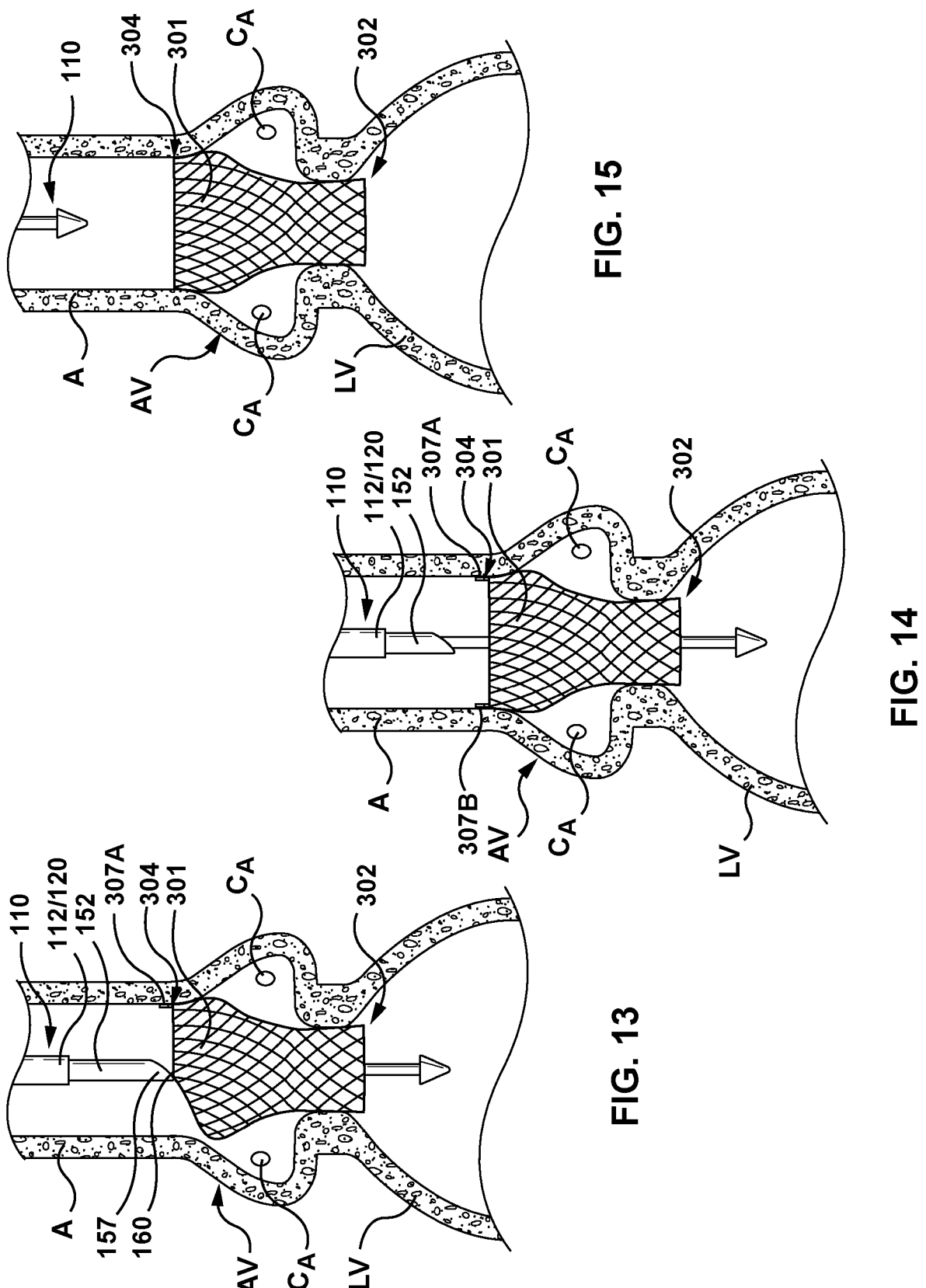
FIG. 13 illustrates a fourth step of a method of using the delivery device of FIG. 1 to deploy the heart valve prosthesis of FIG. 3, wherein one connector of the self-expanding prosthesis is exposed and released from a spindle due to rotation of the control release shaft.
FIG. 14 illustrates a fifth step of a method of using the delivery device of FIG. 1 to deploy the heart valve prosthesis of FIG. 3, wherein both connectors of the self-expanding prosthesis are exposed and released from a spindle due to rotation of the control release shaft.
FIG. 15 illustrates a sixth step of a method of using the delivery device of FIG. 1 to deploy the heart valve prosthesis of FIG. 3, wherein the heart valve prosthesis is shown in the fully deployed or expanded configuration following deployment at the target treatment site and the delivery device is being removed.

As the control release shaft 152 is rotated and retracted, the connectors 307A, 307B individually and sequentially disengage or detach from the delivery device 110. In FIG. 13, the control release shaft 152 has been rotated and retracted such that the sloped distal edge 160 thereof has passed over and exposed the first connector 307A of the heart valve prosthesis 301. The control release shaft 152 and the collar 157 are rotated and retracted via the first actuator 142 of the handle 140. Once exposed, the first connector 307A is released from the spindle 108. The first connector 307A, as well as the endmost crowns 303B adjacent to the first connector 307A, are permitted to self-expand or partially self-expand. At this stage of deployment, the outer sheath 112 and the capsule 120 can no longer be distally advanced to recapture the heart valve prosthesis 301.

As shown in FIG. 14, the control release shaft 152 is rotated and retracted until both connectors 307A, 307B are released from the spindle 108. The control release shaft 152 and the collar 157 are rotated and retracted via the first actuator 142 of the handle 140. When both connectors 307A, 307B are exposed or uncovered, all of the endmost crowns 303B are released from the delivery device 110 and permitted to self-expand. More particularly, when the sloped distal edge 160 is disposed proximal to the recesses 111A, 111B of the spindle 108, the connectors 307A, 307B of the heart valve prosthesis 301 are no longer held within the recesses 111A, 111B of the spindle 108 and the second end 304 of the heart valve prosthesis 301 is permitted to self-expand to its deployed configuration. Thus, once the control release shaft 152 is rotated and retracted to the point that both connectors 307A, 307B of the self-expanding prosthesis 101 are released from the spindle 108, the heart valve prosthesis 301 is fully deployed and released from the delivery device 110. By incrementally and individually exposing the endmost crowns 303B and connectors 307A, 307B, the release of energy that occurs as the endmost crowns 303B are permitted to self-expand is staggered or spread out and the self-expanding prosthesis 101 does not move or tilt when fully released from the delivery device 110. As shown in FIG. 15, after deployment of the heart valve prosthesis 301 is complete, the delivery device 110 is then removed and the heart valve prosthesis 301 remains deployed within the native target heart valve.

Figures 16, 17:
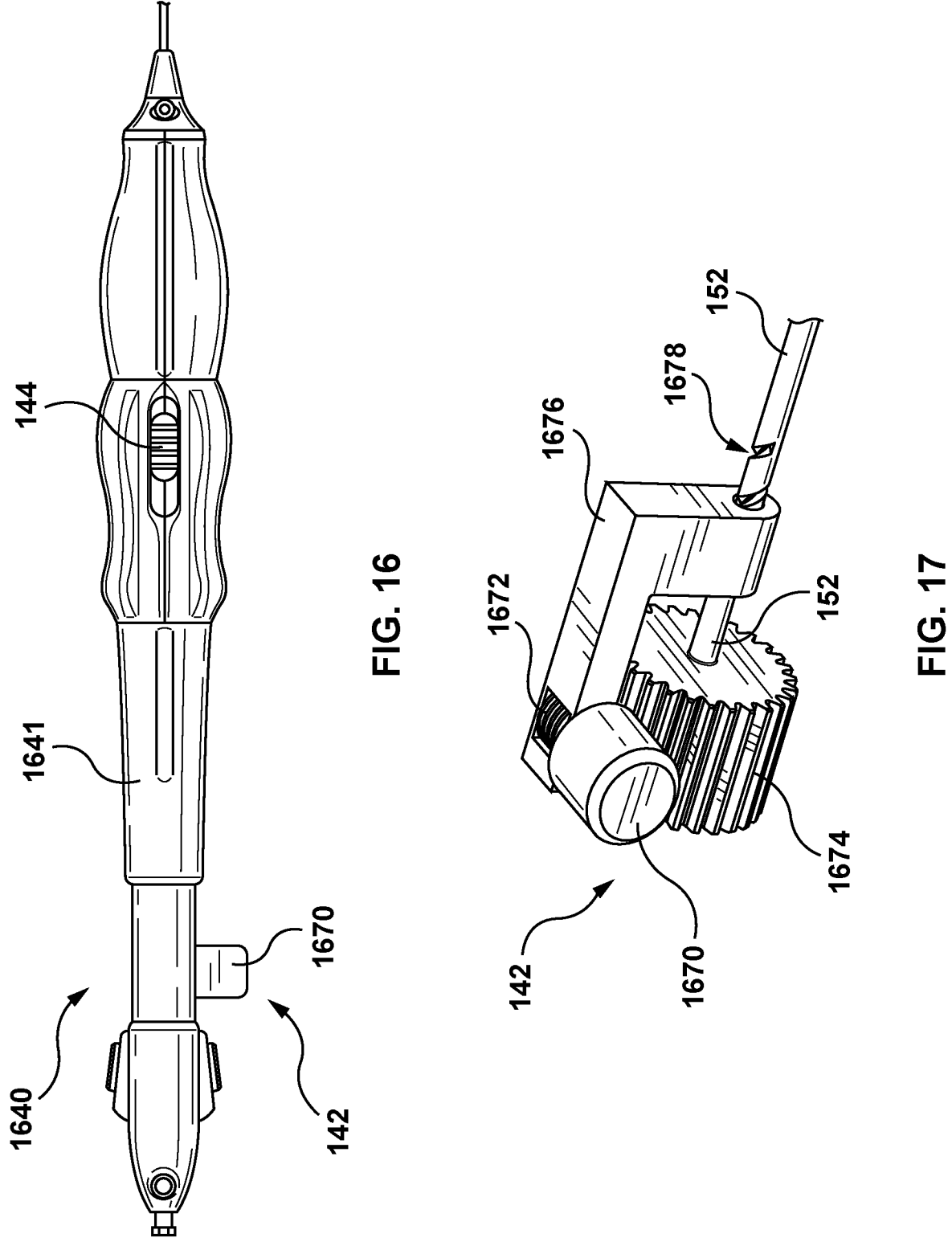
FIG. 16 is a side perspective view of a handle for use in embodiments hereof.
FIG. 17 is an enlarged perspective view of a first actuator of the handle of FIG. 16, wherein the first actuator is removed from a housing of the handle for illustrative purposes only.

FIGS. 16-19 illustrate an exemplary first actuator 142 that is configured for rotating and simultaneously proximally retracting the control release shaft 152 for uncovering the second end 104 of the self-expanding prosthesis 101. FIG. 16 illustrates an exemplary handle 1640 that may be used as the handle 140. The handle 1640 includes the first and second actuators 142, 144, respectively. FIG. 17 is an enlarged perspective view of the first actuator 142, with the housing 1641 of the handle 1640 removed for sake of illustration only. The first actuator 142 includes a rotatable knob 1670 that is accessible to the user for rotation thereof, a first gear 1672 attached to the rotatable knob 1670 such that it rotates therewith, a second gear 1674 that mates with the first gear 1672 and is disposed within the housing 1641 of the handle 1640, and a housing 1676 coupled to the first gear 1672 and further constrained to the housing 1641 of the handle 1640. The control release shaft 152 includes a cam slot or groove 1678 formed on an outer surface thereof that extends through the housing 1676. In an embodiment the cam slot 1678 is helical. The housing 1676 houses the first gear 1672 as well as an internal cam driver (not shown) that is configured to mate with the cam slot 1678.

The rotatable knob 1670 protrudes from the housing 1641 of the handle 1640 at an angle of approximately ninety degrees. In operation, the rotatable knob 1670 is turned or rotated in order to rotate the first gear 1672 attached or fixed thereto. In turn, when the first gear 1672 rotates, the second gear 1674 also rotates at a reduced rate or speed as compared to the first gear 1672 due to the relatively larger size thereof. The proximal end 154 of the control release shaft 152 is attached to the first gear 1672 and rotates therewith.

Figures 18, 19:
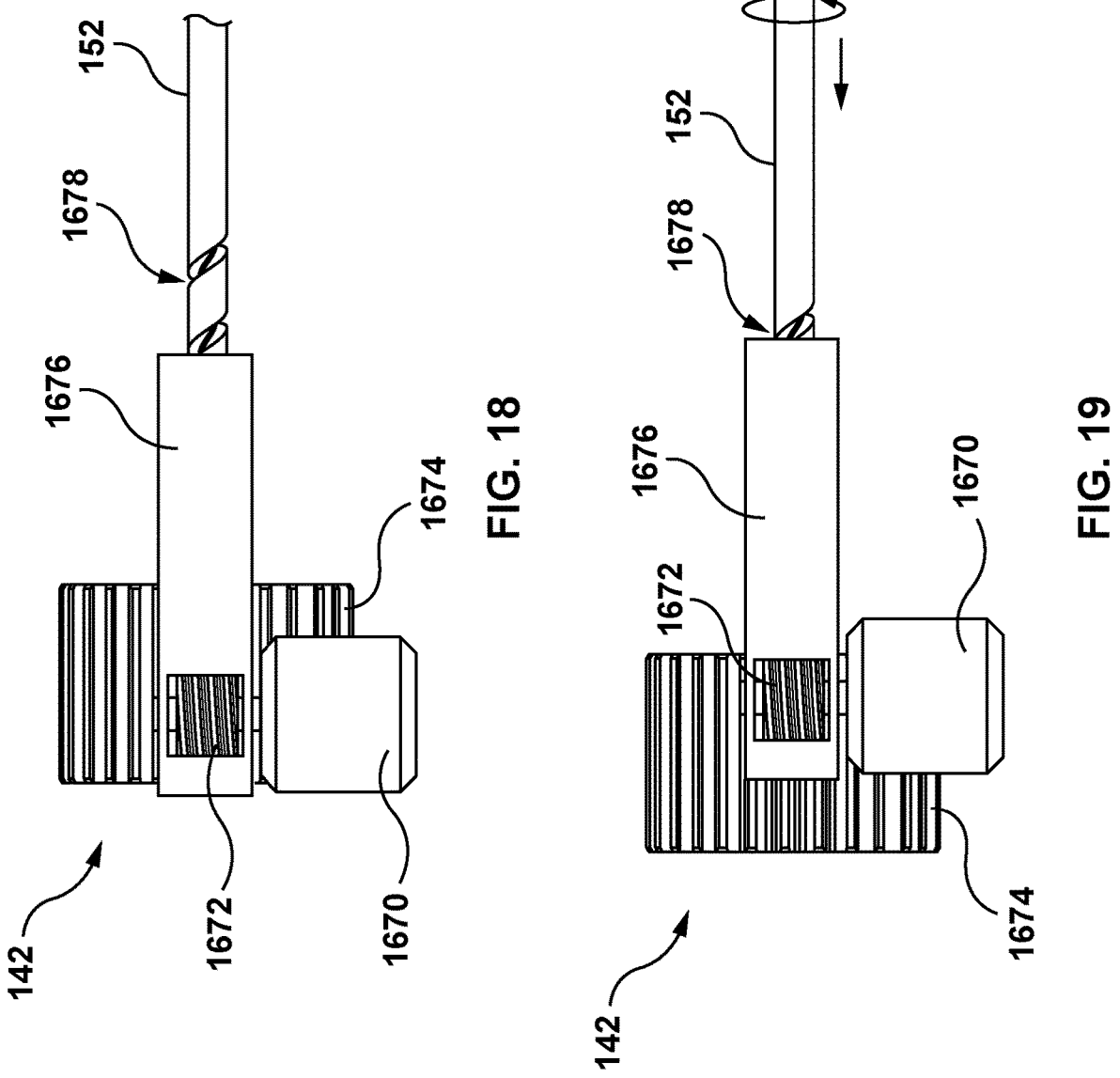
FIG. 18 is a top view illustration of the first actuator of FIG. 17 prior to actuation thereof.
FIG. 19 is a top view illustration of the first actuator of FIG. 17 after actuation thereof.

In order to simultaneously proximally retract the control release shaft 152 during rotation thereof, the cam driver of the housing 1676 interacts or mates with the cam slot 1678 of the control release shaft 152. The housing 1676 is attached or fixed to the housing 1641 of the handle, thereby constraining movement thereof relative to the control release shaft 152. When the control release shaft 152 rotates with the second gear 1674, the cam slot 1678 interfaces with the cam driver of the housing 1676. More particularly, the cam driver is a tang or protrusion extends radially inwards from an inner surface of the housing 1676 and extends into the cam slot 1678. When the control release shaft 152 and the cam slot 1678 thereon rotates, the cam driver of the housing 1676 extends within the cam slot 1678. Since the housing 1676 is attached or fixed to the housing 1641 of the handle and thus is prevented from rotating with the control release sleeve 152, rotation of the cam slot 1678 formed on the control release shaft 152 causes linear motion of the control release shaft 152 as best shown on FIGS. 18-19. More particularly, FIG. 18 illustrates a top view illustration of the first actuator 142 prior to actuation thereof with the cam slot 1678 distally extending from the housing 1676. As the rotatable knob 1670 is turned, the control release shaft 152 rotates and is proximally retracted as the cam slot 1678 is drawn into the housing 1676 (due to the cam driver of the housing 1676 extending into the cam slot 1678 during rotation of the control release shaft 152) as shown in the top view illustration of FIG. 19. The control releases shaft 152 and the second gear 1674 proximally retract as an assembly relative to the housing 1676, the first gear 1672, and the rotatable knob 1670. Thus, actuation of the first actuator 142 results in simultaneous rotation and proximal retraction of the control release sleeve 152.

Embodiments described above include an additional intermediate shaft, i.e., control release shaft 152, that includes the collar 157 having the sloped distal edge 160 thereon for controlled gradual release of a second end of a self-expanding prosthesis. The control release shaft 152 is rotatable and is disposed between the outer sheath 112 and the pusher shaft 122 having the spindle 108 at a distal end thereof. However, the collar 157 having the sloped distal edge 160 thereon may be incorporated into a different component of the delivery device 110. For example, in another embodiment, the collar 157 having the sloped distal edge 160 may be incorporated onto outer sheath 112 and the capsule 120. The outer sheath 112 may be configured to be proximally retracted to expose most of the length of the self-expanding prosthesis, and may be configured to be rotated once only the collar 157 having the sloped distal edge 160 cover the second end of the self-expanding prosthesis.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A delivery device for percutaneously delivering a self-expanding prosthesis, the self-expanding prosthesis having a first end and a second end, the second end being proximal to the first end when the self-expanding prosthesis is loaded onto the delivery device, the delivery device comprising:
a handle having at least one actuator thereon;
a control release shaft having a proximal end operatively coupled to the handle and a distal end including a collar having a sloped distal edge, wherein the control release shaft is rotatable via actuation of the at least one actuator of the handle in order to rotate the collar; and
a pusher shaft disposed within the control release shaft, the pusher shaft having a proximal end operatively coupled to the handle and a distal end having a spindle coupled thereto, the spindle being configured to receive at least one connector extending from at least one endmost crown of the self-expanding prosthesis in order to releasably attach the self-expanding prosthesis to the pusher shaft,
wherein, when disposed over the second end of the self-expanding prosthesis, the collar is configured to radially restrain the endmost crowns and the at least one connector of the self-expanding prosthesis, and
wherein actuation of the at least one actuator of the handle rotates and proximally retracts the collar relative to the spindle to achieve incremental release of the endmost crowns and the at least one connector of the self-expanding prosthesis.

2. The delivery device of claim 1, further comprising:
an outer sheath including a proximal end operatively coupled to the handle and a distal portion that is configured to compressively restrain the self-expanding prosthesis during delivery, wherein the control release shaft is disposed within the outer sheath and the outer sheath is retractable relative to the control release shaft.

3. The delivery device of claim 2, wherein the handle includes a first actuator and a second actuator, the first actuator being configured to rotate the control release shaft and the second actuator being configured to proximally retract the outer sheath.

4. The delivery device of claim 2, wherein the at least one actuator of the handle is configured to rotate and simultaneously proximally retract the control release shaft.

5. The delivery device of claim 1, further comprising:
an inner shaft disposed within the pusher shaft, the inner shaft having a distal portion that is configured to receive the self-expanding prosthesis thereon.

6. The delivery device of claim 5, wherein the inner shaft is configured to be tracked over a guidewire.

7. The delivery device of claim 1, wherein the sloped distal edge of the collar is helical.

8. The delivery device of claim 1, wherein the at least one connector includes a first connector and a second connector, the first connector and the second connector being disposed at opposing positions of the self-expanding prosthesis, and wherein the spindle includes a first recess that is configured to receive the first connector and a second recess that is configured to receive the second connector.

9. The delivery device of claim 1, wherein the control release shaft includes a coil embedded into a polymeric material.

10. The delivery device of claim 9, wherein the collar is disposed distal to the coil.

11. The delivery device of claim 10, wherein the collar is formed of the polymeric material.

12. The delivery device of claim 10, wherein the collar is formed from a material that is different than the polymeric material.

13. A system comprising:

a self-expanding prosthesis having a first end and a second end, wherein the self-expanding prosthesis includes a plurality of endmost crowns at the second end thereof and at least one connector extending from at least one endmost crown; and a delivery device configured to percutaneously deliver the self-expanding prosthesis, the second end being proximal to the first end when the self-expanding prosthesis is loaded onto the delivery device, the delivery device including a handle having at least one actuator thereon;

a control release shaft having a proximal end operatively coupled to the handle and a distal end including a collar having a sloped distal edge, wherein the control release shaft is rotatable via actuation of the at least one actuator of the handle in order to rotate the collar; and a pusher shaft disposed within the control release shaft, the pusher shaft having a proximal end operatively coupled to the handle and a distal end having a spindle coupled thereto, the spindle being configured to receive the at least one connector of the self-expanding prosthesis in order to releasably attach the self-expanding prosthesis to the pusher shaft, wherein, when disposed over the second end of the self-expanding prosthesis, the collar is configured to radially restrain the endmost crowns and the at least one connector of the self-expanding prosthesis, and wherein actuation of the at least one actuator of the handle rotates and proximally retracts the collar relative to the spindle to achieve incremental release of the endmost crowns and the at least one connector of the self-expanding prosthesis.

14. The system of claim 13, wherein the self-expanding prosthesis is a heart valve prosthesis.

15. The system of claim 13, further comprising:

an outer sheath including a proximal end operatively coupled to the handle and a distal portion that is configured to compressively restrain the self-expanding prosthesis during delivery, wherein the control release shaft is disposed within the outer sheath and the outer sheath is retractable relative to the control release shaft.

16. The system of claim 13, further comprising:

an inner shaft disposed within the pusher shaft, the inner shaft having a distal portion that is configured to receive the self-expanding prosthesis thereon.

17. The system of claim 13, wherein the sloped distal edge of the collar is helical.

18. The system of claim 13, wherein the at least one connector includes a first connector and a second connector, the first connector and the second connector being disposed at opposing positions of the self-expanding prosthesis, and wherein the spindle includes a first recess that is configured to receive the first connector and a second recess that is configured to receive the second connector.

19. A delivery device for percutaneously delivering a self-expanding prosthesis, the self-expanding prosthesis having a first end and a second end, the second end being proximal to the first end when the self-expanding prosthesis is loaded onto the delivery device, the delivery device comprising:

a handle having at least one actuator thereon;

an outer sheath including a proximal end operatively coupled to the handle and a distal portion that is configured to compressively restrain the self-expanding prosthesis during delivery, wherein the outer sheath is retractable relative to the self-expanding prosthesis;

a control release shaft disposed within the outer sheath, the control release shaft having a proximal end operatively coupled to the handle and a distal end including a collar having a sloped distal edge, wherein the control release shaft is rotatable via actuation of the at least one actuator of the handle in order to rotate the collar;

a pusher shaft disposed within the control release shaft, the pusher shaft having a proximal end operatively coupled to the handle and a distal end having a spindle coupled thereto, the spindle being configured to receive at least one connector extending from at least one endmost crown of the self-expanding prosthesis in order to releasably attach the self-expanding prosthesis to the pusher shaft; and an inner shaft disposed within the pusher shaft, the inner shaft having a distal portion that is configured to receive the self-expanding prosthesis thereon, wherein, when disposed over the second end of the self-expanding prosthesis, the collar is configured to radially restrain the endmost crowns and the at least one connector of the self-expanding prosthesis, and wherein actuation of the at least one actuator of the handle rotates and proximally retracts the collar relative to the spindle to achieve incremental release of the endmost crowns and the at least one connector of the self-expanding prosthesis.

20. The delivery device of claim 19, wherein the sloped distal edge of the collar is helical.

* * * * *